United States Patent [19]

Eichenberger et al.

[11] 4,144,344
[45] Mar. 13, 1979

[54] ANTIHYPERTENSIVE 1-SUBSTITUTED-4-(2-OXO-1-IMIDAZOLIDI-NYL) PIPERIDINES

[75] Inventors: Kurt Eichenberger, Therwil; Hans Kühnis, Basel; Franz Ostermayer, Riehen; Herbert Schröter, Füllinsdorf, all of Switzerland

[73] Assignee: Ciba-Geigy Corporation, Ardsley, N.Y.

[21] Appl. No.: 761,510

[22] Filed: Jan. 21, 1977

[30] Foreign Application Priority Data

Jan. 21, 1976 [CH] Switzerland .................. 702/76

[52] U.S. Cl. ........................... 424/267; 546/194; 546/201; 546/210; 546/141; 546/143; 546/162; 546/153; 546/265; 546/273; 546/278; 424/251; 424/258; 544/238; 544/295; 544/296; 544/316; 544/319; 544/328; 544/329; 544/331; 544/332; 544/336; 544/357; 544/405; 544/408

[51] Int. Cl.² .............. A61K 31/445; C07D 401/04; C07D 401/14

[58] Field of Search ................ 260/293.7, 293.62; 548/317, 318, 322

[56] References Cited

U.S. PATENT DOCUMENTS

| 3,459,757 | 8/1969 | Wright et al. | 260/293.7 |
| 3,956,335 | 5/1976 | Wilhelm et al. | 260/293.7 |

*Primary Examiner*—Natalie Trousof
*Assistant Examiner*—Richard A. Schwartz
*Attorney, Agent, or Firm*—John J. Maitner

[57] ABSTRACT

A process known per se for the manufacture of oxygenated N-aryl-diazacyclic compounds of the formula

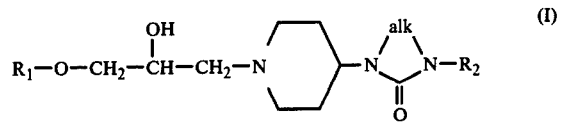

wherein
each of $R_1$ and $R_2$ represents a substituted or unsubstituted aryl group and alk represents a lower alkylene group which separates both nitrogen atoms from each other by 2 or 3 carbon atoms, or salts thereof.

The novel compounds can be used as antihypertensives, antitachycardiac agents and α-receptor blockers.

10 Claims, No Drawings

ANTIHYPERTENSIVE 1-SUBSTITUTED-4-(2-OXO-1-IMIDAZOLIDINYL) PIPERIDINES

The invention relates to novel oxygenated N-aryl-diazacyclic compounds of the formula

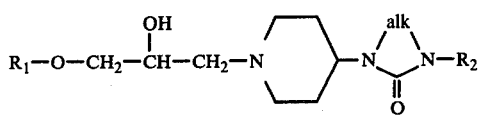

wherein each of $R_1$ and $R_2$ represents a substituted or unsubstituted aryl group and alk represents a lower alkylene group which separates both nitrogen atoms from each other by 2 or 3 carbon atoms, and the salts thereof, as well as to a process for their manufacture and also to pharmaceutical preparations which contain these compounds and to their use, preferably in the form of pharmaceutical preparations. An aryl group $R_1$ or $R_2$ is a carbocyclic or heterocyclic, preferably monocyclic and also bicyclic, aryl group.

A substituted or unsubstituted carbocyclic aryl group is preferably a phenyl group which can, for example, be mono-, di- or polysubstituted, and also a corresponding unsaturated or partially saturated naphthyl group, such as 1- or 2-naphthyl, whilst a substituted or unsubstituted heterocyclic aryl group is primarily a corresponding preferably monocyclic and also bicyclic azaaryl group having 1 to 2 ring nitrogen atoms which can, for example, be mono-, di- or polysubstituted, such as pyridyl, for example 2-, 3- or 4-pyridyl, imidazolyl, for example 2-imidazolyl, pyrimidinyl, for example 2- or 4-pyrimidinyl, pyridazinyl, for example 3-pyridazinyl, pyrazinyl, for example 2-pyrazinyl, indolyl, for example 4-indolyl, quinolyl, for example 4-quinolyl, or isoquinolyl, for example 1-isoquinolyl.

Substituents, chiefly of a carbocyclic aryl group, in particular of a phenyl group, include substituted or unsubstituted hydrocarbon radicals, such as substituted or unsubstituted lower alkyl, for example lower alkyl, optionally etherified or esterified hydroxy-lower alkyl, such as hydroxy-lower alkyl, lower alkoxy-lower alkyl or halogen-lower alkyl; or substituted or unsubstituted, for example acylated, amino-lower alkyl, such as lower alkanoyl-amino-lower alkyl or lower alkoxycarbonylamino-lower alkyl, or lower alkenyl or lower alkinyl, optionally etherified or esterified hydroxyl or mercapto, such as hydroxy, lower alkoxy which is unsubstituted or substituted for example by aryl, by optionally etherfied or esterified hydroxyl or mercapto or by acyl, for example lower alkoxy, phenyl-lower alkoxy, hydroxy-lower alkoxy, lower alkoxy-lower alkoxy, lower alkylthio-lower alkoxy, halogen-lower alkoxy or lower alkanoyl-lower alkoxy, or lower alkenyloxy, lower alkinyloxy, lower alkylthio or halogen, acyl, such as esterified carboxyl, for example lower alkanoyl or lower alkoxycarbonyl, amidated carboxyl, for example substituted or unsubstituted carbamoyl, cyano, nitro or substituted or unsubstituted, such as acylated, amino, for example lower alkanoylamino, lower alkoxycarbonylamino, substituted or unsubstituted ureido, in addition N-lower alkylamino or N,N-di-lower alkylamino. Substituents of a heterocyclic aryl group are, for example, substituted or unsubstituted lower alkyl or optionally etherified or esterified hydroxyl or mercapto.

Lower alkylene represented by alk is preferably unbranched lower alkylene and primarily ethylene, and also 1,3-propylene, but can also be branched lower alkylene, such as 1,2-propylene, 1,2- or 2,3-butylene.

The groups and compounds qualified by the term "lower" used hereinbefore contain preferably not more than 7, and most preferably not more than 4, carbon atoms.

Lower alkyl is for example methyl, ethyl, n-propyl, iso-propyl, n-butyl, iso-butyl or tert.-butyl. Substituted lower alkyl is in particular corresponding methyl or 1- or 2-ethyl.

Lower alkenyl is for example vinyl, allyl, 2-, or 3-methalyl or 3,3-dimethylallyl.

Lower alkinyl is in particular propargyl.

Lower alkoxy is for example methoxy, ethoxy, n-propyloxy, iso-propyloxy, n-butyloxy or iso-butyloxy.

Phenyl-lower alkoxy is for example benzyloxy or 1- or 2-phenylethoxy.

Lower alkenyloxy is for example allyloxy, 2- or 3-methallyloxy or 3,3-dimethylallyloxy.

Lower alkinyloxy is in particular propargyloxy.

Lower alkylthio is for example methylthio, ethylthio, n-propylthio or iso-propylthio.

Halogen is preferably halogen with an atomic number not greater than 35, viz. fluorine, chlorine or bromine.

Lower alkanoyl is for example acetyl, propionyl or butyryl.

Lower alkoxycarbonyl is for example methoxycarbonyl or ethoxycarbonyl.

Substituted or unsubstituted carbamoyl if for example carbamoyl, or N-lower alkylcarbamoyl or N,N-di-lower alkylcarbamoyl, such as N-methyl-carbamoyl, N,N-dimethylcarbamoyl, N-ethylcarbamoyl or N,N-diethylcarbamoyl.

Lower alkanoylamino is for example acetylamino or propionylamino.

Lower alkoxycarbonylamino is for example methoxycarbonylamino or ethoxycarbonylamino.

Substituted or unsubstituted ureido is for example ureido or 3-lower alkyl- or 3-cycloalkyl-ureido, wherein cycloalkyl contains for example 5 to 7 ring members, for example 3-methylureido, 3-ethylureido or 3-cyclohexylureido.

N-lower alkylamino and N,N-di-lower alkylamino are for example methylamino, ethylamino, dimethylamino or diethylamino.

Hydroxy-lower alkyl is preferably hydroxymethyl or 1-hydroxyethyl and chiefly 2-hydroxyethyl.

Lower alkoxy-lower alkyl is preferably lower alkoxymethyl or 1-lower alkoxyethyl and chiefly 2-lower alkoxyethyl, for example methoxymethyl, ethoxymethyl, 2-methoxy-ethyl or 2-ethoxy-ethyl.

Halogen-lower alkyl is preferably halogen-methyl, for example trifluoromethyl.

Lower alkanoylamino-lower alkyl is in particular lower alkanoylamino-methyl or 1-lower alkanoylamino-ethyl and chiefly 2-lower alkanoylamino-ethyl, for example acetylamino-methyl, 2-acetylamino-ethyl or 2-propionylamino-ethyl.

Lower alkoxycarbonylamino-lower alkyl is in particular lower alkoxycarbonylaminomethyl, or 1-lower alkoxycarbonylamino-ethyl and chiefly 2-alkoxycarbonylamino-ethyl, for example methoxycarbonylaminomethyl, 2-methoxycartionylamino-ethyl or 2-ethoxycarbonylamino-ethyl.

Phenyl-lower alkoxy is in particular benzyloxy, but can also be 1- or 2-phenylethoxy.

Lower alkoxy-lower alkoxy is, inter alia, lower alkoxymethoxy or 1-lower alkoxyethoxy and, in particular, 2-lower alkoxyethoxy, for example methoxymethoxy, 2-methoxyethoxy or 2-ethoxyethoxy.

Lower alkylthio-lower alkoxy is in particular lower alkylthiomethoxy or 1-alkylthioethoxy and in particular 2-lower alkylthioethoxy, for example 2-methylthioethoxy or 2-ethylthioethoxy.

Halogen-lower alkoxy is in particular 2-halogenoethoxy, for example 2-chloroethoxy.

Lower alkanoyl-lower alkoxy is for example lower alkanoylmethoxy or 1- or 2-lower alkanoylethoxy, for example acetylmethoxy.

The novel compounds can be in the form of their salts, for example their acid addition salts and chiefly of their pharmaceutically acceptable non-toxic acid addition salts. Examples of suitable salts are those with inorganic acids, such as hydrohalic acids, for example hydrochloric acid or hydrobromic acid; sulphuric acids, for example sulphuric acid; or phosphoric acids; or with organic acids, such as aliphatic, cycloaliphatic, aromatic or heterocyclic carboxylic or sulphonic acids, for example formics, acetic, propionic, succinic, glycolic, lactic, malic, tartaric, citric, ascorbic, maleic, hydroxymaleic, pyruvic, fumaric, benzoic, 4-aminobenzoic, 4-aminobenzoic, anthranilic, 4-hydroxybenzoic, salicylic, 4-aminosalicyclic, embonic, methanesulphonic, ethanesulphonic, 2-hydroxythanesulphonic, ethylenesulphonic, toluenesulphonic, naphthalenesulphonic or sulphanilic acid.

The novel compounds of the present invention can be in the form of mixtures of isomers, such as racemates, or of pure isomers, for example optically active antipodes.

The novel compounds possess valuable pharmacological properties. For example they possess a hypotensive action as can be demonstrated in animal tests, for example in i.v. administration in doses of approx. 0.03 to approx. 10 mg/kg to narcotised cats. In addition, the novel compounds effect an antitachycardiac action, as can also be demonstrated in animal tests, for example in in vitro tests at concentrations of approx. 0.3 to approx. 10 $v$/ml in guinea pig hearts (Langendorff preparation), and an $\alpha$-receptor blocking effect, for example in in vitro tests at concentrations of approx. 0.001 to approx. 0.1 $v$/ml in rats [isolated perfused mesenteric arterial preparation; in a modification of the method of McGregor, J. Physiol., Vol. 177, p. 21 (1965)]. The novel compounds can therefore be used as antihypertensives, antitachycardiac agents and $\alpha$-receptor blockers. Furthermore, the novel compounds can be used as starting materials or intermediates for the preparation of other, in particular therapeutically active, compounds.

The invention provides principally compounds of the formula I, wherein each of $R_1$ and $R_2$ represents a substituted or unsubstituted, mono- or bicyclic, carbocyclic aryl group or a substituted or unsubstituted monocyclic heteroaryl or benzoheteroaryl group having 1 or 2 ring nitrogen atoms, substituents of a carbocyclic aryl group being those selected from the group consisting of substituted or unsubstituted lower alkyl, for example lower alkyl, hydroxy-lower alkyl, lower alkoxy-lower alkyl, halogen-lower alkyl, lower alkanoylamino-lower alkyl, lower alkoxycarbonylamino-lower alkyl, or lower alkenyl, lower alkinyl, optionally etherified or esterified hydroxyl or mercapto, for example hydroxyl, lower alkoxy, hydroxy-lower alkoxy, phenyl-lower alkoxy, lower alkoxy-lower alkoxy, lower alkylthio-lower alkoxy, halogen-lower alkoxy, lower alkanoyl-lower alkoxy, lower alkenyloxy, lower alkinyloxy, lower alkylthio, or halogen, acyl, for example lower alkanoyl, lower alkoxycarbonyl, carbamoyl, N-lower alkylcarbamoyl or N,N-di-lower alkylcarbamoyl, cyano, nitro and/or unsubstituted or substituted, such as acylated, amino, for example amino, N-lower alkylamino, N,N-di-lower alkylamino, lower alkanoylamino, lower alkoxycarbonylamino, ureido, 3-lower alkylureido or 3-cycloalkylureido, and substituents of a heterocyclic aryl or benzoaryl group being those selected from the group consisting of substituted or unsubstituted lower alkyl, for example lower alkyl, or optionally etherified or esterified hydroxyl or mercapto, for example lower alkoxy, lower alkylthio, and/or halogen, and alk has the meaning given above, and salts, in particular acid addition salts, primarily pharmaceutically acceptable, non-toxic acid addition salts thereof.

The invention provides in particular compounds of the formula I, wherein $R_1$ represents phenyl or naphthyl which is unsubstituted or substituted by a member selected from the group consisting of lower alkyl, for example methyl, lower alkoxy-lower alkyl, such as 2-lower alkoxy-ethyl, for example 2-methoxyethyl, lower alkoxycarbonylamino-lower alkyl, such as 2-lower alkoxycarbonylamino-ethyl, for example 2-methoxycarbonylamino-ethyl, lower alkenyl, for example allyl, hydroxyl, lower alkoxy, for example methoxy, phenyl-lower alkoxy, for example benzyloxy, lower alkoxy-lower alkoxy, such as 2-lower alkoxy-ethoxy, for example 2-methoxyethoxy, lower alkylthio-lower alkoxy, such as 2-lower alkylthio-ethoxy, for example 2-methylthioethoxy, lower alkanoyl-lower alkoxy, such as lower alkanoylmethoxy, for example acetylmethoxy, lower alkenyloxy, for example allyloxy, lower alkinyloxy, for example propargyloxy, lower alkylthio, for example methylthio, halogen, for example chlorine or bromine, lower alkanoyl, for example acetyl, lower alkoxycarbonyl, for example methoxycarbonyl or ethoxycarbonyl, carbamoyl, N-lower alkyl- or N,N-di-lower alkylcarbamoyl, for example N-methylcarbamoyl or N,N-dimethylcarbamoyl, cyano, nitro, lower alkanoylamino, for example acetylamino, lower alkoxycarbonylamino, for example methoxycarbonylamino, 3-lower alkylureido, for example 3-methylureido, and/or 3-cycloalkylureido, for example 3-cyclohexylureido, or represents diazaaryl having 6 ring members which is unsubstituted or substituted by a member selected from the group consisting of lower alkyl, for example methyl, lower alkoxy, for example methoxy, lower alkylthio, for example methylthio or ethylthio and/or halogen, for example pyrazinyl, $R_2$ represents phenyl or naphthyl which is unsubstituted or substituted by a member selected from the group consisting of lower alkyl, for example methyl, halogen-lower alkyl, for example trifluoromethyl, lower alkoxy, for example methoxy, halogen, for example chlorine or bromine, lower alkanoyl, for example acetyl, lower alkoxycarbonyl, for example methoxycarbonyl or ethoxycarbonyl, carbamoyl, N-lower alkylor N,N-di-lower alkylcarbamoyl, for example N-methylcarbamoyl or N,N-dimethylcarbamoyl, nitro and/or N,N-di-lower alkylamino, for example dimethylamino or diethylamino, or represents monocyclic or bicyclic mono- or diazaaryl which is unsubstituted or substituted by a member selected from the group consisting of lower alkyl, for example methyl, lower alkoxy, for example methoxy, and/or halogen, for example chlorine or bromine, such as pyridyl, for example 2-, 3- or 4-pyridyl, quinolinyl or isoquinolinyl, for example 4-quinolinyl or 1-isoquinolinyl, imidazolyl, for example pyrimidinyl, for example 2- or 4-pyrimidinyl, pyridazinyl, for example 3-pyridazinyl, or pyrazinyl, for example 2-pyrazinyl, and alk represents lower alkylene of 2 to 3 carbon atoms which separates both nitrogen atoms by 2 to 3 carbon atoms, for example ethylene or 1,3-propylene, and salts, in particular acid addition salts, chiefly pharmaceutically acceptable, non-toxic acid addition salts thereof.

The invention provides more particularly compounds of the formula I, wherein $R_1$ represents phenyl which is unsubstituted or substituted by a member selected from the group consisting of lower alkyl, for example methyl, lower alkenyl, for example allyl, hydroxyl, lower alkoxy, for example methoxy, phenyl-lower alkoxy, for example benzyloxy, lower alkanoyl-lower alkoxy, for example acetylmethoxy, lower alkenyloxy, for example allyloxy, lower alkinyloxy, for example propargyloxy, halogen, for example chlorine or bromine, and/or cyano whilst one substituent can be in any position, preferably however in the ortho-position, to the linkage ring carbon atom of the phenyl radical, or represents 2-pyrazinyl which is unsubstituted or substituted by a member selected from the group consisting of lower alkyl, for example methyl, lower alkoxy, for example methoxy, lower alkylthio, for example methylthio or ethylthio, and/or halogen, for example chlorine or bromine, whilst one substituent can be in any position, preferably however in the ortho-position, to the linkage ring carbon atom of the pyrazinyl radical, and $R_2$ represents phenyl or naphthyl which is unsubstituted or substituted by a member selected from the group consisting of lower alkyl, for example methyl, trifluoromethyl, lower alkoxy, for example methoxy, and/or halogen, for example chlorine or bromine, furthermore by lower alkanoyl, for example acetyl, lower alkoxycarbonyl, for example methoxycarbonyl or ethoxycarbonyl, carbamoyl, nitro and/or N,N-di-lower alkylamino, for example dimethylamino or diethylamino, or represents pyridyl which is unsubstituted or substituted by a member selected from the group consisting of lower alkyl, for example methyl, lower alkoxy, for example methoxy, and/or halogen, for example chlorine or bromine, for example 2-, 3- or 4-pyridyl, and also represents corresponding pyrimidyl, for example 2- or 4-pyrimidinyl, pyridazinyl, for example 3-pyridazinyl or 2-pyrazinyl, and alk represents lower alkylene of 2 to 3 carbon atoms which separates both nitrogen atoms by 2 to 3 carbon atoms, for example ethylene or 1,3-propylene, and salts, in particular acid addition salts, primarily pharmaceutically acceptable, non-toxic acid addition salts thereof.

Particularly preferred compounds are those of the formula I wherein $R_1$ represents phenyl which is substituted in the ortho-position by a member selected from the group consisting of lower alkyl, for example methyl, lower alkenyl, for example allyl, lower alkoxy, for example methoxy, hydroxyl, benzyloxy, lower alkenyloxy, for example allyloxy, lower alkinyloxy, for example propargyloxy, lower alkanoyl-lower alkoxy, for example acetylmethoxy, halogen, for example chlorine or bromine, or cyano, $R_2$ represents phenyl which is unsubstituted or substituted by a member selected from the group consisting of lower alkyl, for example methyl, trifloromethyl, lower alkoxy, for example methoxy, halogen, for example chlorine or bromine, lower alkanoyl, for example acetyl, lower alkoxycarbonyl, for example methoxycarbonyl, carbamoyl, nitro and/or di-lower alkylamino, for example dimethylamino, or represents pyridyl which is unsubstituted or substituted by lower alkyl, for example methyl, or lower alkoxy, for example methoxy, for example 2- or 4-pyridyl, and alk represents ethylene, and salts, in particular acid addition salts, primarily pharmaceutically acceptable, non-toxic acid addition salts thereof.

The most preferred compounds are those of the formula I wherein $R_1$ represents phenyl which is substituted in the ortho-position by a member selected from the group consisting of lower alkyl, for example methyl, lower alkenyl, for example allyl, lower alkenyloxy, for example allyloxy, halogen, for example chlorine or bromine, cyano or, in particular, lower alkoxy, for example methoxy, $R_2$ represents phenyl which is unsubstituted or substituted by a member selected from the group consisting of lower alkyl, for example methyl, lower alkoxy, for example methoxy, or halogen, for example chlorine or bromine, or represents pyridyl, in particular 4-pyridyl, and alk represents ethylene, and salts, in particular acid addition salts, primarily pharmaceutically acceptable, nontoxic acid addition salts thereof.

The novel compounds are obtained by methods which are known per se. Thus, for example, a compound of the formula

$$R_1-O-X_1 \qquad (II)$$

or a salt thereof, can be reacted with a compound of the formula

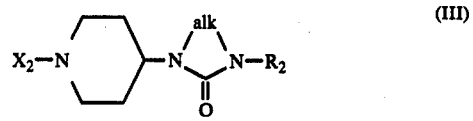

(III)

or with a salt thereof, wherein one of the radicals $X_1$ and $X_2$ represents hydrogen and the other corresponds to the radical of the formula

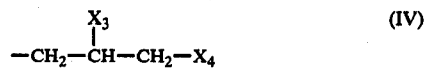

$$\begin{array}{c} X_3 \\ | \\ -CH_2-CH-CH_2-X_4 \end{array} \qquad (IV)$$

wherein $X_3$ represents a free hydroxyl group and $X_4$ represents a reactive esterified hydroxyl group, or wherein $X_3$ and $X_4$ together form an epoxy group, and, if desired, a resultant compound can be converted into another compound of the formula I, and/or, if desired, a resultant free compound converted into a salt, and/or, if desired, a resultant salt converted into the free compound or into another salt, and/or, if desired, a resultant isomeric mixture separated into the individual isomers.

The procedure which can be followed in carrying out the above reaction comprises for example reacting a compound of the formula

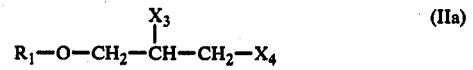

$$\begin{array}{c} X_3 \\ | \\ R_1-O-CH_2-CH-CH_2-X_4 \end{array} \qquad (IIa)$$

with a compound of the formula

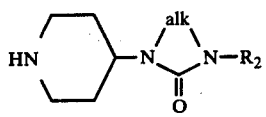

or reacting a compound of the formula R₁—OH (IIIb) with a compound of the formula

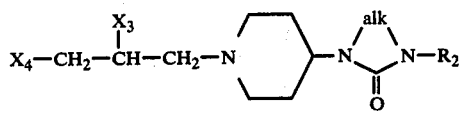

wherein either X₃ represents a free hydroxyl group and X₄ represents a reactive esterified hydroxyl group, or wherein X₃ and X₄ together represent an epoxy group.

A reactive esterified hydroxyl group X₄ is a hydroxyl group which is esterified by a strong inorganic or organic acid, preferably a hydrohalic acid, for example hydrochloric, hydrobromic or hydroiodic acid, also sulphuric acid, or by an organic sulphonic acid, such as an aromatic sulphonic acid, benzenesulphonic acid, 4-bromobenzenesulphonic acid or 4-toluenesulphonic acid. Provided it does not form an epoxy group together with X₃, X₄ therefore represents in particular chlorine or bromine, and also iodine.

The above reaction is carried out in the customary manner. When using a reactive ester as starting material of the formula (IIa), the process is preferably carried out in the presence of a basic condensation agent and/or with an excess of the basic compound of the formula (IIIa).

If a reactive ester of the formula (IIb) is used as starting material, the compound of the formula (IIIb) is preferably used in the form of a salt, such as a metal salt, in particular an alkali metal salt, for example a sodium or potassium salt, or the process is carried out in the presence of an acid acceptor, in particular of a condensation agent which is able to form a salt with the compound of the formula (IIIb), such as an alkali metal lower alkanoate.

The above reaction is carried out in the absence, or preferably in the presence, of a preferably inert solvent or diluent, and, if necessary, with cooling or heating, for example in a temperature range between approx. 0° C. and approx. 150° C., in a closed vessel and/or in an inert gas atmosphere, for example in an atmosphere of nitrogen.

The starting materials are known or they can be obtained in a manner known per se. For example, piperidine-4-one, wherein the secondary amino group can be protected in a manner known per se, for example by a benzyl group or an easily removable acyl radical, can be reacted with a diamine of the formula H₂N-alk-HN-R₂ (V) and simultaneously or subsequently treated with a suitable reducing agent, such as catalytically activated hydrogen or with a hydride reducing agent, for example sodium cyanoborohydride. The 2-oxo-1,3-diazacycloalkane radical is formed in the intermediate thereby obtained by, for example, treatment with a suitable reactive derivative of carbonic acid, such as di-lower alkylcarbonate or phosgene. If necessary, a N-protective group can be replaced in a manner known per se by hydrogen. A starting material of the formula (IIIa) thereby obtained can be converted into a starting material of the formula (IIb) in a manner known per se, for example by treatment with a reactive ester of 2,3-epoxy-1-propanol, such as a 2,3-epoxy-1-propylhalide, and, if desired, by subsequent reaction with a strong acid, such as hydrohalic acid.

The novel compounds can also be obtained by converting X₅ into a hydroxyl group in a compound of the formula

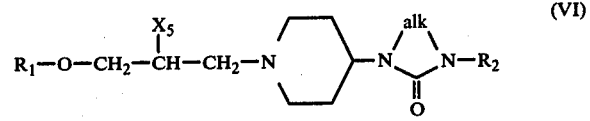

wherein X₅ represents a group which can be converted into a hydroxyl group, and if desired, carrying out the additional process steps.

In a starting material of the formula (VI), X₅ is in particular an esterified hydroxyl group and chiefly an acyloxy group, wherein acyl represents the corresponding radical of an organic carboxylic acid, such as a lower alkanecarboxylic acid, for example an acetyl, propionyl or pivolyl, or of an aromatic carboxylic acid, for example benzoyl.

The conversion of X₅ into a hydroxyl group is effected by hydrolysis and the process is carried out in an alkaline or acid medium. It is carried out in the absence or presence of solvents or diluents, and, if necessary, with cooling or heating, for example in a temperature range between approx. 0° C. and approx. 120° C., in a closed vessel and/or in an inert gas atmosphere.

The starting materials of the formula (VI) can be obtained for example by converting X₃ into an acyloxy group in a compound of the formula (IIa), wherein X₃ represents a hydroxyl group and X₄ represents a reactive esterified hydroxyl group, for example by acylation with a reactive derivative such as an optionally mixed anhydride or an organic carboxylic acid, and the intermediate thereby obtained, preferably an excess thereof, is reacted with a compound of the formula (IIIa).

The novel compounds can also be obtained by reducing the pyridinium ring in a compound of the formula

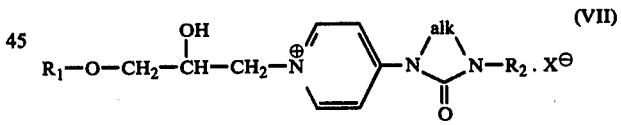

wherein X⊖ represents an anion, to give the piperidine ring, and, if desired, carrying out the additional process steps.

An anion X⊖ is in particular that of an acid, preferably of a mineral acid, such as a hydrohalic acid, for example hydrochloric or hydrobromic acid, or of a suitable organic carboxylic or sulphonic acid.

The above reaction can be carried out in conventional manner, preferably by means of catalytic hydrogenation, such as with hydrogen in the presence of a suitable hydrogenation catalyst, for example a heavy metal catalyst, for example a palladium, platinum or Raney nickel catalyst, or by treatment with nascent hydrogen, such as by treatment with an alkali metal, for example sodium or potassium, in the presence of an alcohol, such as a lower alkanol, for example ethanol or n-butanol.

Moreover, the reaction, in which care must be taken that other reducible groups remain intact, can also take place stepwise, since partially saturated pyridine compounds, for example 1,2,5,6-tetrahydropyridine compounds, can be formed as intermediates, which can be converted into the desired piperidine compounds by treatment with the same reducing agent, optionally under different conditions, or with another reducing agent.

The above reaction is carried out in the absence, and in particular in the presence, of a solvent or diluent, and if necessary, with cooling or heating, for example in a temperature range between approx. 0° C. and approx. 120° C., in a closed vessel and/or in an inert gas atmosphere.

The starting materials can be prepared in a manner known per se by, for example, reacting 4-amino-pyridine with a compound of the formula

(which is obtained for example by treating an amino compound of the formula $H_2N-R_2$ (IX) with an acid halide of the formula $Hal_1\text{-}alk_o\text{-}C(=O)\text{-}Hal_2$(X), wherein each of $Hal_1$ and $Hal_2$ represents a halogen atom, for example a chlorine atom) and $alk_o$ corresponds to the lower alkylene group alk which contains one carbon atom less in the chain. The carbonyl group in the intermediate thereby obtained of the formula

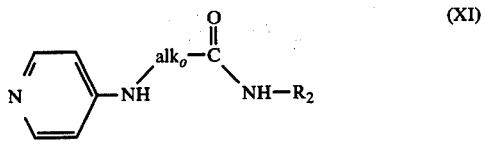

is reduced to the methylene group, for example by treatment with lithium aluminium hydride, and the 2-oxo-1,3-diazacycloalkane ring is formed, for example by treatment with phosgene. The resultant 4-(2-oxo-3-$R_2$-1,3-diazacycloalk-1-yl)-pyridine compound is then reacted with a compound of the formula IIa, wherein $X_3$ represents a hydroxyl group and $X_4$ represents a reactive esterified hydroxyl group, and in particular halogen.

The novel compounds of the formula I can also be obtained by forming the 2-oxo-1,3-diazacycloalkane ring in a compound of the formula

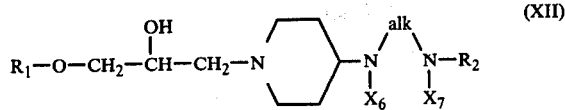

wherein one of the radicals $X_6$ and $X_7$ represents a hydrogen atom and the other represents the acyl radical of a hemiderivative of carbonic acid, cyclisation, and, if desired, carrying out the additional process steps.

In a starting material of the formula (XII), the acyl radical of a hemiderivative of carbonic acid represents the corresponding radical of a carbonic acid hemiester, such as lower alkoxycarbonyl, for example methoxycarbonyl or ethyoxycarbonyl, of a carbonic acid hemihalide, for example chlorocarbonyl or bromocarbonyl, or of a carbonic acid hemiamide, for example carbamoyl.

The cyclisation is carried out in the absence or presence of a solvent or diluent, and, if necessary, in the presence of a preferably basic condensation agent, for example a hydroxide, carbonate, hydrogen carbonate or lower alkanoate of an alkali metal or alkaline earth metal, and of an organic base of the pyridine type, with cooling or preferably heating, for example in a temperature range between approx. 20° to approx. 150° C., in a closed vessel and/or in an inert gas atmosphere.

The starting material of the formula (XII) is prepared by methods known per se, and preferably in situ by reacting a compound of the formula XII, wherein each of $X_6$ and $X_7$ represents a hydrogen atom, with a reactive derivative of carbonic acid. Reactive derivatives of carbonic acid are corresponding esters, such as a di-lower alkylcarbonate, for example diethyl carbonate, or halides, for example phosgene, furthermore amides, for example urea or carbonyldiimidazole, and also halogenated carbonic acid esters, for example isobutyl chlorocarbonate, or halides, for example the chloride, of carbamic acid.

The reaction is carried out in conventional manner, ordinarily in the presence of an inert solvent, preferably an optionally halogenated aliphatic or aromatic hydrocarbon, for example chloroform or toluene, furthermore of an amide or nitrile, for example dimethyl formamide, dimethyl acetamide or acetonitrile, or of a cycloaliphatic ether, such as dioxane and tetrahydrofurane. The reaction is preferably carried out in the presence of a condensation agent, in particular of a basic agent, such as hydroxide, carbonate or hydrogen carbonate of an alkali metal or alkaline earth metal, for example sodium or potassium hydroxide, sodium or potassium carbonate or sodium or potassium hydrogen carbonate, or of an alkali metal lower alkanoylate, for example sodium acetate, or of an alkali metal lower alcoholate, for example sodium methanolate or potassium tert.-butanolate, or of an organic tertiary nitrogen base, such as a tri-lower alkylamine, for example trimethylamine or triethylamine, or pyridine.

A compound of the formula (XII), wherein each of $X_6$ and $X_7$ represents a hydrogen atom, can be obtained for example by reacting piperidine-4-one with a compound of the formula (IIa), wherein $X_3$ represents a hydroxyl group and $X_4$ represents a reactive esterified hydroxyl group, in particular halogen, and subsequently reacting the intermediate thereby obtained with a diamine of the formula (V), with simultaneous or subsequent treatment with a reducing agent, such as catalytically activated hydrogen or with a suitable hydride reducing agent, for example cyanoborohydride.

The novel compounds of the formula I can also be obtained by converting $X_8$ into the oxo group in a compound of the formula

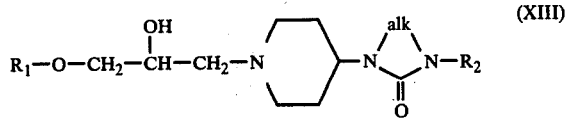

wherein $X_8$ represents a radical which can be converted into the oxo group, and, if desired, carrying out the additional process steps.

The radical $X_8$ is for example imino. A corresponding starting material of the formula (XIII) can be converted into the corresponding compound of the formula I by hydrolysis, preferably in the presence of an acid agent, such as a mineral acid, for example hydrochloric acid.

The above reaction is carried out in the absence, or preferably in the presence of a solvent or diluent, and, if necessary, with cooling or heating, for example in a temperature range between approx. 0° to approx. 150° C., in a closed vessel and/or in an inert gas atmosphere.

The starting materials of the formula (XIII) can be obtained in a manner known per se, for example by treating a compound of the formula (XII), wherein each of the radicals $X_6$ and $X_7$ represents a hydrogen atom, with a halocyanogen, for example bromocyanogen, preferably in the presence of a suitable, for example basic, condensation agent, with simultaneous or subsequent cyclisation to give the 2-imino1,3-diazacycloalkene ring of the starting material of the formula (XIII).

Within the scope of the end products, substituents in resultant compounds can be split off, introduced or converted in a manner known per se.

Thus in compounds of the formula I with unsaturated substituents, for example lower alkenyl, lower alkenyloxy or lower alkinyloxy, it is possible to reduce these substituents by suitable reduction methods to give saturated compounds, or to reduce substituents with a triple bond to give compounds with a double bond. Catalytically activated hydrogen is preferably used as reducing agent, whilst a chemical reducing agent, such as sodium in the presence of liquid ammonia, is also used for the reduction of a triple bond.

In a compound of the formula I, which contains a halogen atom, such as a bromine or iodine atom, as substituent of an aromatic radical, it is also possible to replace the halogen atom by a trifluoromethyl group by, for example, treatment with trifluoromethyl iodide in the presence of copper powder and a suitable aprotic solvent, such as pyridine, dimethyl formamide or acetonitrile.

In a compound of the formula I, an α-phenyl-lower alkyl group, for example in a benzyloxy group, can be split off by treating the corresponding compound with catalytically activated hydrogen, and, for example, a benzyloxy group can be replaced by hydroxy by means of hydrogen.

Furthermore, in a compound of the formula I, which contains hydroxyl or mercapto in the form of a primary carbinol or a phenolic hydroxyl group as substituent, said substituent can be converted into an etherified hydroxyl or mercapto group by treating the compound, optionally in the form of a salt, for example an alkali metal salt, with a reactive ester of an alcohol, such as an optionally substituted lower alkyl halide. In addition, a hydroxyl group in a hydroxy-lower alkyl or hydroxy-lower alkoxy substituent, usually in the form of a reactive esterified hydroxyl group, can be reacted with an alcohol, for example a lower alkanol, or with a mercaptan, for example a lower alkylmercaptan, preferably in the presence of a base which is capable of converting for example an alcohol or a mercaptan into a metal compound, and in this way it is possible to obtain compounds of the formula I, which contain hydroxyl or etherified hydroxylor mercapto-lower alkyl or mercapto-lower alkoxy groups.

In a compound of the formula I it is possible to convert a propargyloxy group into the acetonyloxy group, for example by hydration in acid medium and in the presence of a mercury(II) salt, for example by treatment with an aqueous mineral acid, for example dilute hydrochloric or sulphuric acid, in the presence of mercury(II) chloride.

Furthermore, in a compound of the formula I, which contains as substituent esterified carboxyl or lower alkoxycarbonylamino, whis substituent can be converted by treatment with ammonia or an amine, preferably with an excess thereof and at elevated temperature, into amidated carboxyl or optionally substituted ureido.

It is also possible in a compound of the formula I, which contains as substituent a primary amino group, to substitute this group. Thus the amino group can be acylated, for example by treating the amino compound with a suitable acid derivative, such as an optionally mixed anhydride, for example a corresponding chloride, if necessary in the presence of a base.

The above described reactions can, if appropriate, be carried out simultaneously or in succession and in any desired sequence and conventional manner, for example in the presence or absence of solvents or diluents, if necessary in the presence of condensation and/or catalytic agents, with cooling or heating, in a closed vessel and/or in an inert gas atmosphere.

Depending on the process conditions and the starting material, the end products are obtained in the free form or in the form of their salts, in particular their acid addition salts, which are also comprised by the present invention. Resultant salts can be converted in known manner into the free compounds, acid addition salts for example by treatment with bases, including suitable ion exchangers. On the other hand, resultant free compounds can form salts, for example by treatment with organic or inorganic acids, In addition, resultant salts, viz. acid addition salts, can be converted into other salts, for example by treatment with suitable heavy metal salts or anion exchangers.

The above mentioned salts or other salts of the novel compounds of the formula I, for example the picrates, can also be used for purifying the resultant free bases by converting the free bases into salt, separating these and once more liberating the bases from the salts. Because of the close relationship between the novel compounds in the free form and in the form of their salts, what is stated in this specification in respect of the free compounds refers also to the corresponding salts, wherever this applies.

Depending on the choice of the starting materials and process methods, the novel compounds are obtained in the form of the racemates or optical antipodes.

Racemates can be separated by means of known methods into the optical antipodes, for example by recrystallisation from an optically active solvent, with the aid of microorganisms or by reaction with an optically active acid which forms salts with the racemic compound and separation of the salts obtained in this way, for example on the basis of their different solubilities, into the diastereomeric salts from which the free antipodes can be liberated by treatment with suitable agents. Particularly suitable optically active acids are for example, the D- and L-forms of tartaric acid, di-toluyltartaric acid, malic acid, mandelic acid, camphorsulphonic acid or guinic acid.

The invention also relates to those modifications of the process in which a compound obtainable in any stage as intermediate is used as starting material and the missing process steps are carried out, or the process is discontinued at any stage, or in which a starting material is formed under the reaction conditions or in which a reaction component is optionally in the form of a derivative for example in the form of a salt.

It is advantageous to use for carrying out the reactions of the present invention those starting materials which result in the groups of end products particularly referred to at the outset and especially in the end products described or singled out for special mention.

The novel compounds can be used for example in the form of pharmaceutical preparations which contain an effective amount of the active substance, if appropriate together with inorganic or organic, solid or liquid pharmaceutically useful carriers suitable for enteral, for example oral, or parenteral administration. Tablets or gelatin capsules are therefore used which contain the active substance together with diluents, for example lactose, dextrose, sucrose, mannitol, sorbitol, cellulose and/or glycin, and lubricants, for example silica, talc, stearic acid or salts thereof, such as magnesium or calcium stearate, and/or polyethylene glycol. Tablets also contain binding agents, for example magnesium aluminium silicate, starches, such as maize, corn, rice or arrow root starch, gelatins, tragacanth, methyl cellulose, sodium carboxymethyl cellulose and/or polyvinyl pyrrolydine, and, if desired, disintegrators, for example starches, agar, alginic acid or a salt thereof, such as sodium alginate, and/or effervescent mixtures, or adsorption agents, dyes, flavouring matters and sweetners. It is also possible to use the novel pharmacologically active compounds in the form of preparations for parenteral administration or of infusion solutions. Such solutions are preferably isotonic aqueous solutions or suspensions which can be manufactured before use, for example from lyophilised preparations that contain the active substance alone or together with a carrier, for example mannitol. The pharmaceutical preparations can be sterilised and/or contain adjuvants, for example preservatives, stabilisers, wetting agents and/or emulsifiers, solubility promoters, salts for regulating the osmotic pressure and/or buffers. The pharmaceutical preparations which, if desired, can contain further pharmacologically useful substances, are manufactured in known manner, for example using conventional mixing, granulating, confectioning, dissolving or lyophilising methods, and they contain from about 0.1% to 100%, especially from about 1% to about 50%, of lyophilisates up to 100% of the active substance. The dosage can depend on a variety of factors, such as mode of application, species, age and/or individual condition. The daily doses for oral administration are between about 1 mg and about 15 mg for warm-blooded animals having a weight of approx. 70 kg.

The invention is illustrated by the follówng Examples.

EXAMPLE 1

With vigorous stirring, a solution of 117 ml of a 20% phosgene solution in toluene is added dropwise at a reaction temperature of 5° to 10° C. to an emulsion of 10 g of 1-[2-hydroxy-3-(2-methoxyphenyloxy)-propyl]-4-(2-anilino-ethylamino)-piperidine in 60 ml of toluene and 37.5 ml of a 3N aqueous sodium hydroxide solution over 1¼ hours. Thereafter 35.5 ml of a 6N aqueous potassium hydroxide solution are added dropwise at the same reaction temperature in the course of half an hour. Stirring is continued for 30 minutes at 5° to 10° C. and for 20 hours at room temperature. The reaction mixture is filtered with suction and the crystalline residue is treated with toluene. Recrystallisation from isopropanol yields 1-{1-[2-hydroxy-3-(2-methoxy-phenyloxy)-propyl]-4-piperidyl}-3-phenyl-imidazolidin-2-one-hydrochloride in the form of white crystals with a melting point of 185°-187° C. The salt can be converted into the free compound for example by treatment with an aqueous sodium hydroxide solution.

The starting material can be prepared as follows:

A mixture of 20 g of the hydrate of 4-piperidone-hydrochloride, 46.8 g of 1-(2-methoxyphenyloxy)-2,3-epoxy-propane, 18 g of potassium carbonate and 250 ml of isopropanol is stirred for 6 hours at a reaction temperature of 60° C. After cooling, the suspension is filtered and the filtrate is evaporated to dryness under reduced pressure. The residue is dissolved in 100 ml of 6N hydrochloric acid and washed with four 75 ml portions of ethyl acetate. The aqueous acid solution is adjusted with a 2N sodium carbonate solution to a pH of 10 and extracted with three 75 ml portions of ethyl acetate. The organic extracts are dried over sodium sulphate and concentrated under reduced pressure. The red residue is dissolved in methanol and the solution is boiled for 30 minutes with the addition of activated charcoal. The solution is filtered and the filtrate is concentrated under reduced pressure. The residue is treated with toluene and recrystallised from a mixture of ethyl acetate and petroleum ether to give 1-[2-hydroxy-(2-methoxyphenyloxy)-propyl]-piperidin-4-one with a melting point of 77°-78° C.

A solution of 16.7 g of 1-[2-hydroxy-3-(2-methoxyphenyloxy)-propyl]-piperidine-4-one and 10.5 g of N-(2-aminoethyl)-aniline in 250 ml of methanol, with the addition of 1 g of a 5% platinum on charcoal catalyst is hydrogenated at room temperature and under normal pressure until 1 molar equivalent of hydrogen has been taken up. The catalyst is thereafter removed by filtration and the filtrate is concentrated under reduced pressure. The residue is freed from excess starting material in a bulb tube at 0.3 mm Hg and 120° C. oven temperature to yield as distillation residue 1-[2-hydroxy-3-(2-methoxyphenyloxy)-propyl]-4-(2-anilino-ethylamino)-piperidine, which can be used without further purification.

EXAMPLE 2

With stirring, 392 ml of an approx. 20% solution of phosgene in toluene are added dropwise at a reaction temperature of 5° to 10° C. in the course of 1 hour to a mixture of 31.5 g of 1-[2-hydroxy-3-(2-methoxyphenyloxy)-propyl]-4-[2-(4-pyridylamino)-ethylamino]-piperidine in 300 ml of toluene and 126 ml of 3N aqueous potassium hydroxide solution. Thereafter 120 ml of a 6N aqueous potassium hydroxide solution are added dropwise at the same temperature in the course of 30 minutes. The reaction mixture is further stirred for 30 minutes at 10° C. and for 20 hours at room temperature. The aqueous acid phase is separated, concentrated to a volume of approx. 50 ml and made alkaline with a concentrated aqueous solution of ammonia. The emulsion is extracted with four 75 ml portions of methylene chloride. The combined methylene chloride phases are dried over sodium sulphate and concentrated. The residue is chromatographed through a column of 800 g of silica gel using a 9:1 mixture of methylene chloride and methanol as eluant. The purified 1-{1-[2-hydroxy-3-(2-methoxyphenyloxy)-propyl]-4-piperidyl}-3-(4-pyridyl)-imidazolidin-2-one is taken up in methanol and the solution is acidified with methanolic hydrochloric acid. The acid solution is concentrated under reduced pressure. The residue is treated with toluene and recrystallised from a mixture of methanol and diethyl ether to yield the 1-{1-[2-hydroxy-3-(2-methoxyphenyloxy)-propyl]-4-piperidyl}-3-(4-pyridyl)-imidazolidin-2-one-dihydrochloride in the form of the hemihydrate; m.p. 230°-234° C.

The starting material can be prepared as follows:

A mixture of 38.9 g of 4-bromo-pyridine-hydrochloride and 480 g of ethylenediamine is refluxed with stirring for 13 hours. The reaction mixture is thereafter concentrated under reduced pressure and the residue is treated with toluene and concentrated once more. The residue is made alkaline with a concentrated aqueous solution of sodium hydroxide and extracted with five 75 ml portions of methylene chloride. The combined extracts are dried over sodium sulphate and concentrated under reduced pressure. Recrystallisation of the residue from methylene chloride yields 4-(2-aminoethylamino)-pyridine as a light yellow crystalline substance with a melting point of 120°–121° C.

A solution of 27.9 g of 1-[2-hydroxy-3-(2-methoxyphenyloxy)-propyl]-piperidin-4-one and 22.8 g of 4-(2-aminoethylamino)-piperidine in 250 ml of methanol, with the addition of 2 g of a platinum on charcoal catalyst, is hydrogenated at room temperature and under normal pressure until 1 molar equivalent has been taken up. The catalyst is thereafter removed by filtration and the filtrate is concentrated under reduced pressure. The residue is dissolved in 500 ml of methylene chloride and the solution is washed with three 150 ml portions of water, dried over sodium sulphate and concentrated under reduced pressure to yield 1-[2-hydroxy-3-(2-methoxyphenyloxy)-propyl]-4-[2-(4-pyridyl-amino)-ethylamino]-piperidine, which can be processed without further purification.

EXAMPLE 3

With vigorous stirring, 630 ml of a 20% solution of phosgene in toluene are added dropwise at a reaction temperature of 5° to 10° C. in the course of 1¾ hours to an emulsion of 56 g of 1-[2-hydroxy-3-(2-methoxyphenyloxy)-propyl]-4-[2-(4-chloroanilino)-ethylamino]-piperidine in 340 ml of toluene and 200 ml of a 3N potassium hydroxide solution. Thereafter 193 ml of a 6N aqueous potassium hydroxide solution are added dropwise at the same reaction temperature in the course of half an hour. The reaction mixture is further stirred for 1 hour at 5° to 10° C. and for 20 hours at room temperature and then concentrated. The residue is made alkaline with a 2N aqueous sodium hydroxide solution and extracted with five 100 ml portions of methylene chloride. The extracts are dried over sodium sulphate and concentrated under reduced pressure. The residue is dissolved in methanol and boiled for 30 minutes with the addition of activated charcoal. The batch is filtered and the filtrate is concentrated under reduced pressure. The residue is treated with toluene and recrystallised from isopropanol to yield 1-{1-[2-hydroxy-3-(2-methoxyphenyloxy)-propyl]-4-piperidyl}-3-(4-chlorophenyl)-imidazolidin-2-one with a melting point of 136°–137° C.

The 1-[2-hydroxy-3-(2-methoxyphenyloxy)-propyl]-4-[2-(4-chloroanilino)-ethylamino]-piperidine can be prepared as follows:

A mixture of 38 g of p-chloroaniline and 31 g of 2-bromoethylamine-hydrobromide is heated to 70° C. with stirring. After 30 minutes 75 ml of diethyl ketone are added and the mixture is refluxed for 4 hours. The black solution is then concentrated under reduced pressure. The residue is made alkaline with 2N sodium carbonate solution and extracted with three 100 ml portions of chloroform. The residual oil is fractionally distilled in vacuo to yield 1-(4-chlorophenyl)-ethylenediamine with a boiling point of 130°–135° C. (1.5 torr).

A solution of 33.5 g of 1-[2-hydroxy-3-(2-methoxyphenyloxy)-propyl]-piperidin-4-one and 20.5 g of 1-(4-chlorophenyl)-ethylenediamine in 300 ml of methanol, with the addition of 1.5 g of a 5% platinum on charcoal catalyst, is hydrogenated at room temperature and under normal pressure until 1 molar equivalent of hydrogen has been taken up. The catalyst is then removed by filtration and the filtrate is concentrated under reduced pressure. The residue is treated with toluene to give the 1-[2-hydroxy-3-(2-methoxyphenyloxy)-propyl]-4-[2-(4-chloroanilino)-amino]-piperidine as a reddish oil which can be used without further purification.

EXAMPLE 4

A mixture of 17.9 g of 1-[4-methoxy-phenyl]-3-(4-piperidyl)-2-imidazolidinone and 11.7 g of 1-(2-methoxyphenyloxy)-2,3-epoxypropane in 200 ml of isopropyl alcohol is refluxed for 6 hours. The mixture is thereafter acidified with 5N methanolic hydrochloric acid and concentrated under reduced pressure. The residue is freed from moisture still adhering to it by treatment with toluene. Recrystallisation of the residue from methanol with the addition of activated charcoal yields the 1-{1-[2-hydroxy-3-(2-methoxyphenoxy)-propyl]-4-piperidyl}-3-(4-methoxy-phenyl)-imidazolidin-2-one-hydrochloride as a white crystalline substance with a melting point of 214°–215° C.

The 1-(4-methoxy-phenyl)-3-(4-piperidyl)-2-imidazolidinone used as starting material can be prepared as follows:

A mixture of 61.5 g of 4-methoxy-aniline and 51.3g of 2-bromoethylamine-hydrobromide in 125 ml of methyl ethyl ketone is refluxed for 5 hours with stirring. The viscous suspension is thereafter evaporated to dryness under reduced pressure. The residue is suspended in 150 ml of isopropanol and then collected by filtration. The filter cake is washed with three 50 ml portions of isopropanol and with two 50 ml portions of diethyl ether. The crystalline product is made alkaline with a concentrated aqueous ammonia solution and extracted with five 50 ml portions of chloroform. The extracts are dried over sodium sulphate and concentrated under reduced pressure. The oily residue crystallises after trituration to give the 1-(4-methoxyphenyl)-ethylenediamine with a melting point of 64° C.

A solution of 33 g of 1-benzyl-4-piperidone and 29 g of 1-(4-methoxy-phenyl)-ethylenediamine in 310 ml of methanol, with the addition of 1 g of a 5% platinum on charcoal catalyst, is hydrogenated at room temperature and under normal pressure until 1 molar equivalent of hydrogen has been taken up. The catalyst is thereafter removed by filtration and the filtrate concentrated. The residue is treated with toluene to yield the 1-benzyl-4-[2-4-methoxy-anilino)-ethylamino]-piperidine as a yellowish oil, which is used without purification.

With vigorous stirring, 87 g of phosgene gas are introduced at 5° to 10° C. in the course of 2½ hours into a mixture of 63 g of 1-benzyl-4-[2-4-methoxy-anilino)-ethylamino]-piperidin in 570 ml of toluene and 285 ml of 2 3N aqueous potassium hydroxide solution. Stirring is continued for a further 2 hours at room temperature and then 252 ml of a 6N aqueous potassium hydroxide solution are added dropwise in the course of 15 minutes, when a slightly exothermic reaction occurs. The reaction mixture is stirred for a further 20 hours at room temperature. Thereafter the organic phase is separated and the alkaline aqueous phase is extracted with two 100 ml portions of toluene. The organic extracts are dried over sodium sulphate and concentrated under reduced pressure. The residue is treated with toluene and recrystallised from isopropanol to yield 1-(1-benzyl-4-piperidyl)-3-(4-methoxy-phenyl)-imidazolidin-2-one with a melting point of 144°–147° C.

A mixture of 44 g of 1-(1-benzyl-4-piperidyl)-3-(4-methoxy-phenyl)-imidazolidin-2-one, 320 ml of methanol, 130 ml of water and 12 g of a conc. aqueous solution of hydrochloric acid, with the addition of 10 g of a palladium on charcoal catalyst, is hydrogenated at 30° to 40° C. and under reduced pressure until 1 molar equivalent of hydrogen has been taken up. Thereafter the catalyst is removed by filtration and the filtrate is concentrated under reduced pressure. The residue is treated with toluene and recrystallised from a mixture of isopropyl alcohol and diethyl ether to yield the 1-(4-methoxyphenyl)3-(4-piperidyl)-2-imidazolidinone with a melting point of 140° C.

EXAMPLE 5

A mixture of 7.1 g of 2-methyl-4-(2,3-epoxy-propyl)-indole and 9.6 g of 1-(4-methoxy-phenyl)-3-(4-piperidyl)-2-imidazolidinone is dissolved in 125 ml of isopropyl alcohol and the solution is refluxed for 6 hours. Thereafter the reaction solution is cooled on an ice bath and the precipitate which has formed is collected by filtration. The crystalline precipitate is dissolved in methyl alcohol and the solution is strongly acidified with 5N methanolic hydrochloric acid. The acid solution is concentrated and the crystalline residue is freed from moisture adhering to it by treatment with toluene. Recrystallisation from methanol-ether yields the 1-{1-[2-hydroxy-3-(2-methyl-1H-indol-4-yloxy)-propyl]-4-piperidyl}-3-(4-methoxyphenyl)-imidazolidin-2-one with a melting point of 155°–157° C.

EXAMPLE 6

7.27 g of 2-chloro-3-(2,3-epoxy-propoxy)-pyrazine and 7.35 g of 1-(4-piperidyl)-3-phenyl-2-imidazolidinone in 120 ml of isopropanol are stirred for 24 hours at approx. 20° C. The reaction mixture is then concentrated in a water jet vacuum. The residue crystallises from ether and yields 1-{1-[2-hydroxy-3-(3-chloropyrazin-2-yloxy)-propyl]-4-piperidinyl}-3-phenyl-imidazolidin-2-one with a melting point of 122°–124° C.

The starting material can be prepared as follows:
9.8 g of N-phenylethylenediamine and 13.9 g of 1-benzyl-4-piperidone are dissolved in 200 ml of methanol and, with the addition of 0.7 g of a 5% platinum on charcoal catalyst, hydrogenated at room temperature and under normal pressure. The calculated amount of hydrogen is taken up after approx. 3 hours. The reaction mixture is filtered to remove the catalyst and concentrated in a water jet vacuum. The residue crystalises from methanol/water to yield 21.4 g of 1-benzyl-4-(2-phenylamino-ethylamino)-piperidino with a melting point of 78°–81° C.

With stirring, 15 g of phosgene are introduced at 5° to 10° C. in the course of 1 hour into a suspension of 10 g of 1-benzyl-4-(2-phenylamino-1-ethylamino)-piperidine in 100 ml of toluene and 48.5 ml of 3N potassium hydroxide solution. After stirring for 2 hours at 5° to 10° C., the reaction mixture is made alkaline with 43 ml of 6N potassium hydroxide solution and brought to room temperature. After it has been stirred for a further 15 hours at room temperature, the reaction mixture is filtered with suction and the residue is recrystallised from isopropanol-methanol to yield 7.2 g of 1-(1-benzyl-4-piperidinyl)-3-phenyl-2-imidazolidinone.

11.1 g of 1-(1-benzyl-4-piperidinyl)-3-phenyl-2-imidazolidinone are dissolved in 85 ml of methanol, 34 ml of water and 3.2 ml of hydrochloric acid (chemically pure), and, with the addition of 1.2 g of a 5% palladium on charcoal catalyst, hydrogenated at room temperature and under normal pressure. The calculated amount of hydrogen has been taken up after approx. 15 hours. The reaction mixture is filtered to remove the catalyst and concentrated in a water jet vacuum. The crystalline residue is treated with 2N sodium carbonate solution and extracted with chloroform. The combined chloroform extracts are dried over sodium sulphate and concentrated in a water jet vacuum to yield 7.6 g of 1-(4-piperidinyl)-3-phenyl-2-imidazolidinone as a colourless oil which crystallises on standing; melting point 123°–124° C.

EXAMPLE 7

With stirring, 10.1 g of 1-{1-[2-hydroxy-3-(3-chloropyrazin-2-yloxy)-propyl]-4-piperidinyl}-3-phenyl-imidazolidin-2-one (see Example 6) and 1.41 g of sodium methylate in 110 ml of methanol are refluxed for 10 hours. The reaction mixture is concentrated in a water jet vacuum. The residue is dissolved in ethyl acetate and extracted with 2N hydrochloric acid. The combined hydrochloric acid extracts are made alkaline with conc. ammonia and extracted with methylene chloride. The combined methylene chloride extracts are washed with water, dried over sodium sulphate and concentrated in a water jet vacuum. The residue crystallises from methylene chloride-ether to yield 1-{1-[2-hydroxy-3-(3-methoxy-pyrazin-2-yloxy)-propyl]-4-piperidinyl}-3-phenyl-imidazolidin-2-one with a melting point of 128°–129° C.

The hydrochloride, which is prepared with methanolic hydrochloric acids, crystallises from methanol-acetone; melting point 209°–210° C.

EXAMPLE 8

5 g of 1-{1-[2-acetoxy-3-(2-methoxyphenyloxy)-propyl]-4-piperidyl}-3-phenyl-imidazolid-1-one in a 2N solution of potassium hydroxide in alcohol are allowed to stand for 12 hours at room temperature. The mixture is thereafter evaporated to dryness and the residue is dissolved in water and extracted with ethyl acetate. The organic solution is dried and concentrated. After addition of methanolic hydrochloric acid, the 1-{1-[2-hydroxy-3-(2-methoxyphenyloxy)-propyl]-4-piperidyl}-3-phenylimidazolidin-2one-hydrochloride crystallises out. After recrystallisation from isopropanol, it melts at 185°–187° C.

EXAMPLE 9

At room temperature, 5 g of 1-{1-[2-hydroxy-3-(2-methoxyphenyloxy)-propyl]-4-pyridinium}-3-phenyl-imidazolidin-2-one-bromide are reduced with 500 mg of sodium borohydride in 55 ml of an alcohol-water mixture (1:1) for 3 hours. The reaction mixture is filtered and the filtrate is evaporated to dryness. The residue is recrystallised from ethyl acetate-petroleum ether to yield 1-{1-[2-hydroxy-3-(2-methoxyphenyloxy)-propyl]-4-(1,2,5,6-tetrahydro-pyridyl}-3-phenyl-imidazolidin-2-one, which is dissolved in alcohol and hydrogenated with platinum oxide as catalyst. After the calculated amount of hydrogen has been taken up, the catalyst is filtered off and the solution is evaporated to dryness. After addition of methanolic hydrochloric acid, the 1-{1-[2-hydroxy-3-(2-methoxyphenyloxy)- propyl]-4-piperidyl}-3-phenyl-imidazolidin-2-one-hydrochloride crystallises out and is purified by recrystallisation from isopropanol. Melting point: 185°–187° C.

EXAMPLE 10

A solution of 5 g of 1-{1-[2-hydroxy-3-(2-methoxyphenyloxy)-propyl]-4-piperidyl}-3-phenyl-2-imino-imidazolidine-hydrochloride in 50 ml of conc. hydrochloric acid and 50 ml of ethanol is refluxed for 8 hours in 50 ml of ethanol. The solution is evaporated to dryness in vacuo and the residue is recrystallised from isopropanol. The 1-{1-[2-hydroxy-3-(2-methoxyphenyloxy)-propyl]-4-piperidyl}-3-phenyl-imidazolidin-2-one-hydrochloride melts at 185°–187° C.

EXAMPLE 11

19.6 g of 1-(4-piperidyl)-3-phenyl-imidazolidin-2-one and 18 g of 1-(2-methoxyphenyloxy)-2,3-epoxy-propane are refluxed for 6 hours in 500 ml of isopropanol. The clear solution is then acidified with methanolic hydrochloric acid and evaporated to dryness. The residue is recrystallised twice from isopropanol. The 1-{1-[2-hydroxy-3-(2-methoxyphenyloxy)-propyl]-4-piperidyl}-3-phenyl-imidazolidin-2-one-hydrochloride melts at 185°–187° C.

The 1-(4-piperidyl)-3-phenyl-imidazolidin-2-one can be prepared as follows:

120 g of phenylethylenediamine and 164.4 g of 1-benzyl-4-piperidone are dissolved in 600 ml of methanol and, after addition of a 5% platinum on charcoal catalyst, hydrogenated at 20°–30° C. and under normal pressure for 11 hours until cessation. The catalyst is removed by suction filtration and the filtrate is evaporated to dryness. The volatile constituent is expelled with toluene and the residue is dissolved in 300 ml of ethanol and crystallised with 150 ml of water. The crystals are collected with suction at 5°–10° C. and washed with two 50 ml portions of ethyl alcohol-water (2:1) and dried. The synthesised 1-benzyl-4-(anilino-ethylamino)-piperidine has a melting point of 88°–91° C.

200 g of 1-benzyl-4-(2-anilino-ethylamino)-piperidine and 2000 ml of toluene and 1940 ml of potassium hydroxide solution are charged into a reaction vessel. The temperature is kept between 5° and 10° C. with a mixture of ice and methanol while 300 g of phosgene are introduced in the course of 3 hours. Thereafter the reaction mixture is stirred for 2 hours at room temperature. During the dropwise addition of 860 ml of potassium hydroxide, the temperature is kept below 25° C. with an ice-bath. The batch is then stirred for 14 hours. The precipitated crystals are collected with suction and dried. The two-phase filtrate is separated in a separating funnel. The toluene phase is dried over 200 g of sodium sulphate, filtered and concentrated. The residue is recrystallied from 400 ml of ethanol to give the 1-(1-benzyl-4-piperidyl)-3-phenyl-imidazolidin-2-one with a melting point of 173°–174° C.

A mixture of 151 g of 1-(1-benzyl-4-piperidyl)-3-phenyl-imidazolidin-2-one, 1100 ml of methanol, 45 g of hydrochloric acid (chemically pure), 500 ml of water and 15 g of palladium on charcoal catalyst is hydrogenated at 30°–35° C. and under normal pressure until the theoretical amount of hydrogen has been taken up. The catalyst is removed by suction filtration and the filtrate is concentrated by rotary evaporation. The residue is dissolved in 200 ml of water, water, solution is made alkaline with 100 ml of conc. ammonia (minimum pH 12) and extracted with five 300 ml portions of methylene chloride. The purified extracts are dried over $Na_2SO_4$ and concentrated. The residual colourless oil crystallises after some time. The 103 g of crystalline substance are dissolved in 600 ml of ethyl acetate under reflux, insoluble material is filtered off hot and the filtrate is concentrated by rotary evaporation to a volume of approx. 500 ml and allowed to crystaise. White crystalls of 1-(4-piperidyl)-2-phenyl-imidazolidin-2-one with a melting point of 123°–125° C. are obtained.

EXAMPLE 12

Tablets containing 20 mg of 1{1-[2-hydroxy-3-(2-methoxyphenyloxy)-propyl]-4-piperidyl}-3-phenyl-imidazolidin-2-one-hydrochloride can be prepared for example as follows:

| Composition (for 10,000 tablets) | |
|---|---|
| 1-{1-[2-hydroxy-3-(2-methoxyphenyloxy)-propyl]-4-piperidyl}-3-phenyl-imidazolidin-2-one-hydrochloride | 200 g |
| lactose | 300 g |
| corn starch | 300 g |
| colloidal silicic acid | 50 g |
| talc | 50 g |
| magnesium stearate | 10 g |
| water | q.s. |

The 1-{1-[2-hydroxy-3-(2-methoxyphenyloxy)-propyl]-4-piperidyl}-3-phenyl-imidazolidin-2-one-hydrochloride is mixed with a portion of the corn starch, with the lactose and the colloidal silicic acid and the mixture is passed through a sieve. A further portion of the corn starch is pasted on a water bath with 5 times the amount of water and the powder mixture is kneaded with the resultant paste until a slightly plastic mass is obtained. This mass is forced through a sieve, dried, and the dry granules are passed through a sieve. The remainder of the corn starch, the talc and the magnesium stearate are then admixed and the resultant mixture is pressed into tablets each weighing 0.1 g with breaking notch.

We claim:

1. Oxygenated N-aryldiazacyclic compounds of the formula

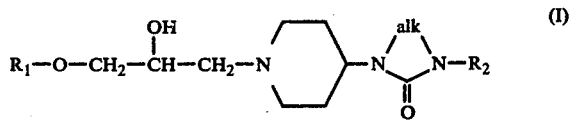

(I)

wherein $R_1$, represents a phenyl or naphthyl group which is unsubstituted or substituted by a member selected from the group consisting of lower alkyl, lower alkoxy-lower alkyl, lower alkoxycarbonylamino-lower alkyl, lower alkenyl, hydroxyl, lower alkoxy, phenol-lower alkoxy, lower alkoxy-lower alkoxy, lower alkylthio-lower alkoxy, lower alkanoyl-lower alkoxy, lower alkenyloxy, lower alkinyloxy, lower alkylthio, halogen, lower alkanoyl, lower alkoxy-carbonyl, carbamoyl, N-lower alkylcarbamoyl, N,N-di-lower alkylcarbamoyl, cyano, nitro, lower alkanoylamino, lower alkoxycarbonylamino, 3-lower alkylureido and/or 3-cycloalkyl-ureido, ore represents pyridyl which is unsubstituted or substituted by a member selected from the group consisting of lower alkyl, lower alkoxy, lower alkylthio and/or halogen, $R_2$ represents a phenyl or naphthyl group which is unsubstituted or substituted by a member selected from the group consisting of lower alkyl, halogen-lower alkyl, lower alkoxy, halogen, lower alkanoyl, lower alkoxycarbonyl, carbamoyl, N-lower alkylcarbamoyl, N,N-di-lower alkylcarbamoyl, nitro and/or di-lower alkylamino, or represents pyridyl which is unsubstituted or substituted by a member selected from the group consisting of lower alkyl, lower alkoxy and/or halogen, and alk represents ethylene, or a pharmaceutically acceptable acid addition salt thereof.

2. Oxygenated N-aryldiazacyclic compounds of the formula I according to claim 1, wherein $R_1$ represents a phenyl group which is unsubstituted or substituted by a member selected from group consisting of lower alkyl, lower alkenyl, hydroxyl, lower alkoxy, phenyl-lower alkoxy, lower alkanoyl-lower alkoxy, lower alkenyloxy, lower alkinyloxy, halogen and/or cyano, $R_2$ represents a phenyl or naphthyl group which is unsubstituted or substituted by a member selected from the group consisting of lower alkyl, trifluoromethyl, lower alkyloxy, halogen, lower alkanoyl, lower alkoxycarbonyl, carbamoyl, nitro and/or N,N-di-lower alkylamino, or represents a pyridyl group which is unsubstituted or substituted by a member selected from the group consisting of lower alkyl, lower alkoxy and/or halogen, and alk represents ethylene.

3. Oxygenated N-aryldiazacyclic compounds of the formula I according to claim 1, wherein $R_1$ represents a phenyl group which is substituted in the ortho-position by a member selected from the group consisting of lower alkyl, lower alkenyl, lower alkoxy, hydroxyl, hydroxy, benzyloxy, lower alkenyloxy, lower alkinyloxy, lower alkanoyl-lower alkoxy, halogen or cyano, $R_2$ represents a phenyl group which is unsubsituted or substituted by a member selected from the group consisting of lower alkyl, trifluoromethyl, lower alkoxy, halogen, lower alkanoyl, lower alkoxycarbonyl, carbamoyl, nitro and/or di-lower alkylamino, or represents a pyridyl group which is unsubstituted or substituted by lower alkyl or lower alkoxy, and alk represents the ethylene group.

4. Oxygenated N-aryldiazacyclic compounds of the formula I according to claim 1, wherein $R_1$ represents phenyl which is substituted in the ortho-position by a member selected from the group consisting of lower alkyl, lower alkenyl, lower alkenyloxy, halogen, cyano or lower alkoxy, $R_2$ represents phenyl which is unsubstituted or substituted by lower alkyl, lower alkoxy or halogen, or represents pyridyl and alk represents the ethylene group.

5. A compound according to claim 1, which is 1-{1-[2-Hydroxy-3-(2-methoxyphenyloxy)-pyropyl]-4-piperidyl}-3-phenyl-imidazolidin-2-one.

6. A compound according to claim 1, which is 1-{1-[2-Hydroxy-3-(2-methoxyphenoxy)propyl]-4-piperidyl}-3-(4-methoxy-phenyl)-imidazolidin-2-one.

7. A pharmaceutical composition useful in the treatment of hypertension in a warmblooded animal comprising a therapeutically effective amount of a compound according to claim 1 or of a pharmaceutically acceptable acid addition salt thereof together with a pharmaceutical carrier.

8. A pharmaceutical composition according to claim 7 which contains 1-{1-[2-hydroxy-3-(2-methoxyphenyloxy)-propyl]-4-piperidyl}-3-phenyl-imidazolidin-2-one, or a pharmaceutically acceptable acid addition salt thereof.

9. A method of treating hypertension in a warm blooded animal which comprises administering to said animal a therapeutically effective amount of a compound according to claim 1, or a pharmacologically acceptable acid addition salt.

10. A method according to claim 9 which comprises administering a therapeutically effective amount of 1-{1-[2-hydroxy-3-(2-methoxyphenyloxy)-propyl]-4-piperidyl}-3-phenyl-imidazolidin-2-one.

* * * * *